United States Patent [19]

Weetall

[11] Patent Number: 4,963,245
[45] Date of Patent: Oct. 16, 1990

[54] UNITARY MULTIPLE ELECTRODE SENSOR

[75] Inventor: Howard H. Weetall, Sharon, Mass.

[73] Assignee: Ciba Corning Diagnostics Corp., Medfield, Mass.

[21] Appl. No.: 492,369

[22] Filed: Mar. 9, 1990

Related U.S. Application Data

[63] Continuation of Ser. No. 859,128, May 2, 1986, abandoned.

[51] Int. Cl.[5] ............................................. G01N 27/327
[52] U.S. Cl. .................................... 204/403; 204/412; 435/7; 435/14; 435/25; 435/817; 436/518; 436/532; 436/535; 436/806
[58] Field of Search ................. 204/403, 412, 415; 436/518, 532, 535, 806; 435/7, 14, 25, 817

[56] References Cited

U.S. PATENT DOCUMENTS

| | | | |
|---|---|---|---|
| 2,776,257 | 1/1957 | Affleck | 204/400 |
| 3,260,661 | 7/1966 | Kemp et al. | 204/197 |
| 4,020,830 | 5/1977 | Johnson et al. | 204/418 |
| 4,100,048 | 7/1978 | Pompei et al. | 204/415 |
| 4,225,410 | 9/1980 | Pace | 435/817 |
| 4,487,676 | 12/1984 | Parker et al. | 204/196 |
| 4,534,356 | 8/1985 | Papadakis | 204/415 |
| 4,545,382 | 10/1985 | Higgins et al. | 204/415 |
| 4,571,292 | 2/1986 | Liu et al. | 204/412 |
| 4,655,880 | 4/1987 | Liu | 204/403 |
| 4,781,798 | 11/1988 | Gough | 204/403 |

OTHER PUBLICATIONS

Robinson et al., *Clin. Chem.*, 31, No. 9, pp. 1449–1452 (1985).

*Primary Examiner*—T. Tung
*Attorney, Agent, or Firm*—Nicholas I. Slepchuk, Jr.

[57] ABSTRACT

A unitary multiple electrode sensor for detecting analytes in blood or blood component samples and devices for using them. The unitary multiple electrode sensor includes a sensor support member and at least one electrode array being deposited on the sensor support member, the electrode array having sensor-activating chemical(s) attached to an embodiment thereof. A test sample is applied to the electrode array to begin the test; and a sensor apparatus measures the test reaction which is occurring on the electrode array.

8 Claims, 3 Drawing Sheets

UNITARY MULTIPLE ELECTRODE SENSOR

This is a continuation of copending application Ser. No. 06/859,128 filed on May 2, 1986.

TECHNICAL FIELD

The present invention relates to electrochemical sensors for detecting analytes and devices for using them. More particularly, the present sensors are unitary multiple electrode devices capable of detecting analytes in serum or blood by detecting redox reactions.

BACKGROUND ART

Sensors for measuring redox reactions are known in the art. U.S. Pat. No. 4,545,382 to I. J. Higgins et al discloses a glucose sensor wherein glucose oxidase is immobilized at the surface of a ferrocene-coated graphite core electrode. In use the tip of the electrode is immersed into the sample fluid and connected to a potentiostat along with a suitable counter electrode and a calomel reference electrode. By keeping the potential of the working electrode at +100 mv to 300 mv relative to the calomel electrode, a current was produced which was proportional to the glucose concentration.

More recently an article by G. A. Robinson et al disclosed a redox electrode useful in electrochemically measuring immunoassays, see *Clin. Chem.*, 31, No. 9, 1449–1452. However, the Robinson electrode had a magnetizable steel rod or bar magnet inside the electrode which contacted a pyrolytic graphite disc. In practice, Robinson constructed a sandwich-type, multiple-antibody immunoassay in which the analyte was bound to both a glucose oxidase conjugate and a separate magnetic solid phase conjugate. A pellet was formed by magnetically separating the sandwich components, when the electrode tip was placed in the solution, and washed twice with a buffer. After the addition of glucose and an electron transfer mediator (ferrocene), the electrode was placed in the solution along with a platinum auxiliary electrode and a calomel reference electrode, and the current was measured.

DISCLOSURE OF THE INVENTION

The present invention relates to a unitary electrochemical sensor for detecting analytes, preferably in serum and blood samples, and an apparatus therefor. In particular, it comprises a sensor support member having an electrically non-conductive surface and at least one spaced electrode array deposited on the surface comprising a working electrode, a counter electrode, and a reference electrode. Unlike the electrodes of the past which were dipped or immersed into a sample, here the sample is deposited on the array.

The sensor apparatus is designed to measure redox reactions occurring on the surface of the electrode array. Thus, it comprises an ammeter having a sensor receiving area designed and configured to receive and hold the support member of the above sensor in a predetermined orientation and position, and a contact means which engages the electrodes on the sensor.

The present sensor and apparatus are suitable for a simple, sensitive, disposable electrochemical assay. Potential applications extend to the detection of enzymes or substrates, clinical chemistry analytes (for example, using creatinine and lactate) and immunological reactions, i.e., immunoassays.

PREFERRED MODES OF THE INVENTION

Preferably, the present sensor is used to measure known redox reactions such as that of oxidizing glucose with glucose oxidase or that of oxidizing reduced nicotinamide adenine dinucleotide (NADH) to AND. In the case of glucose, the flavo-enzyme glucose oxidase oxidizes glucose to gluconate and hydrogen peroxide in the presence of oxygen or an electron transfer mediator, such as benzoquinone or ferrocene. The electron transfer mediator is reoxidized at an electrode surface by an applied potential. Thus, measurement of the current is a direct measurement of enzyme activity, which, of course, is proportional to the substrate concentration.

Figure 1:
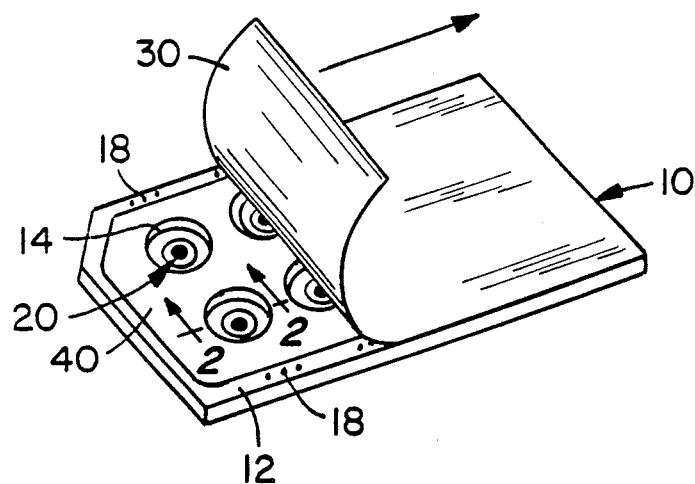
FIG. 1 is a top view of the present sensor.
Figure 2:
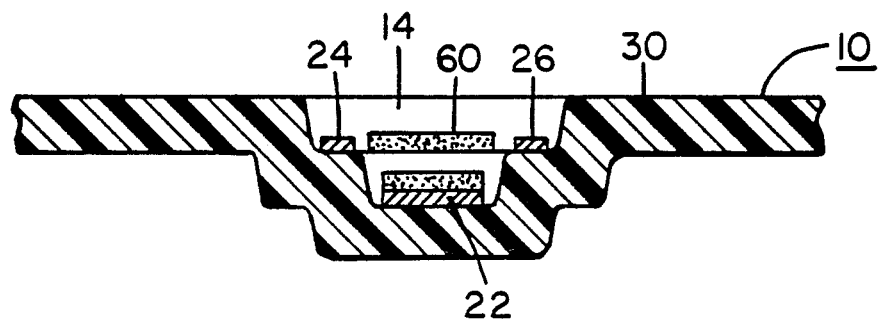
FIG. 2 is a cross-sectional view of an electrode array.

A preferred construction of the sensor itself (10) can be seen in FIGS. 1 and 2. The sensor support member (12) is planar having a plurality of wells (14). Suitable materials for this member are fluorohydrocarbons (Teflon$^R$), glass, plastic polymers, or even cellulosic materials such as paper. The two requirements are that the surface on which the electrodes and the sample are placed must be electrically non-conductive and substantially non-absorbent. Thus, a metal member must be coated with an insulator, and a cardboard member must be coated with a non-absorbent material.

Figure 3:
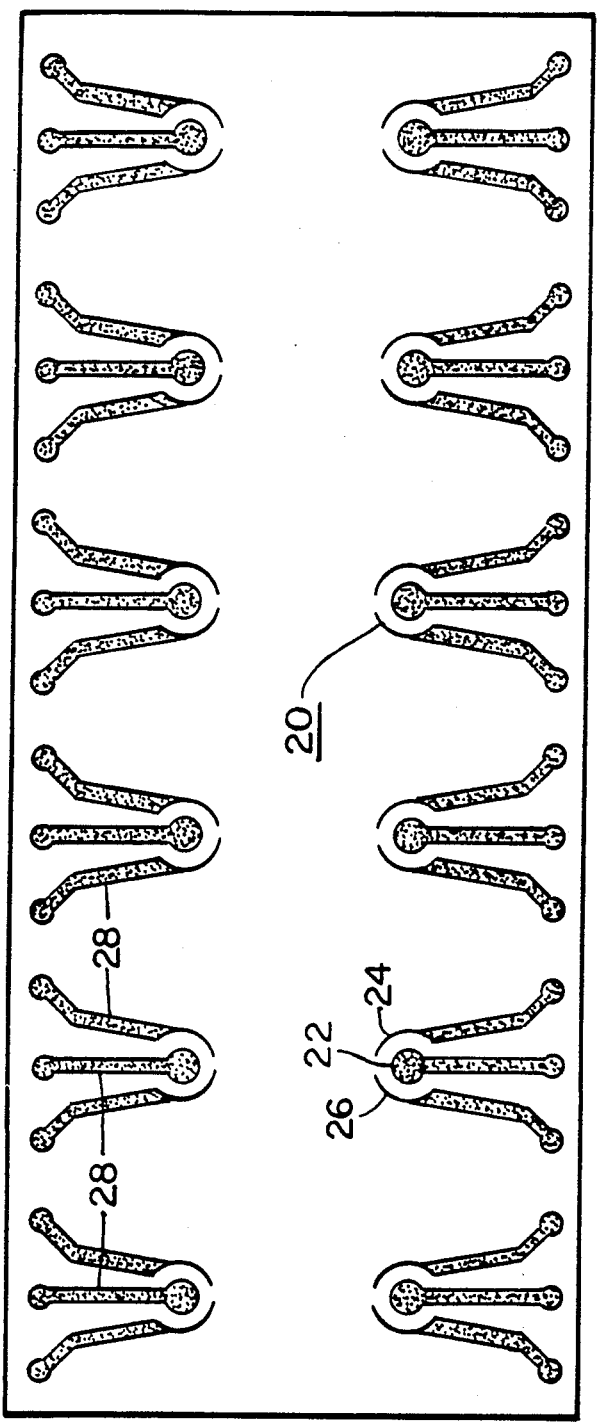
FIG. 3 is a top view of another embodiment of the present sensor without a coating.
Figure 4:
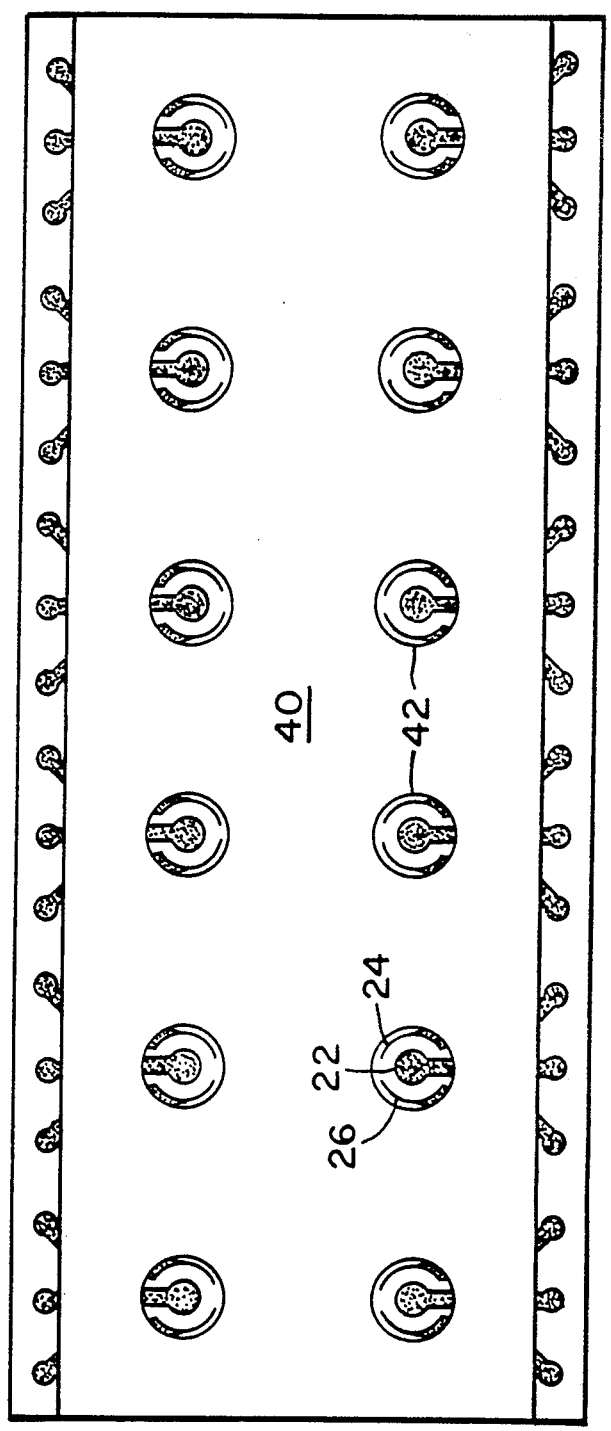
FIG. 4 is a top view of another embodiment of the present sensor in FIG. 3 that has been coated.

The electrode array (20) may be deposited within the well or, if wells are not used, simply laid onto the support member surface. FIGS. 2 and 3 illustrate the structure of an electrode array. Three graphite electrodes are silk-screened onto the support member. In the center is a circular working electrode (22) surrounded on either side by a separate, arcuate counter electrode (24) and a separate reference electrode (26). In the case of the sensor with wells, the electrodes are separated not only horizontally but vertically, the working electrode being at the bottom of the well. Sensors without wells, as in FIGS. 3 and 4, may have a non-conductive layer (40) silk-screened or otherwise covered about the array so as to define a sampling area (42). In either case, the electrode leads (28) are deposited so as to connect the array to a point on the support member (18) which is electrically contacted by the apparatus therefor.

Figure 5:
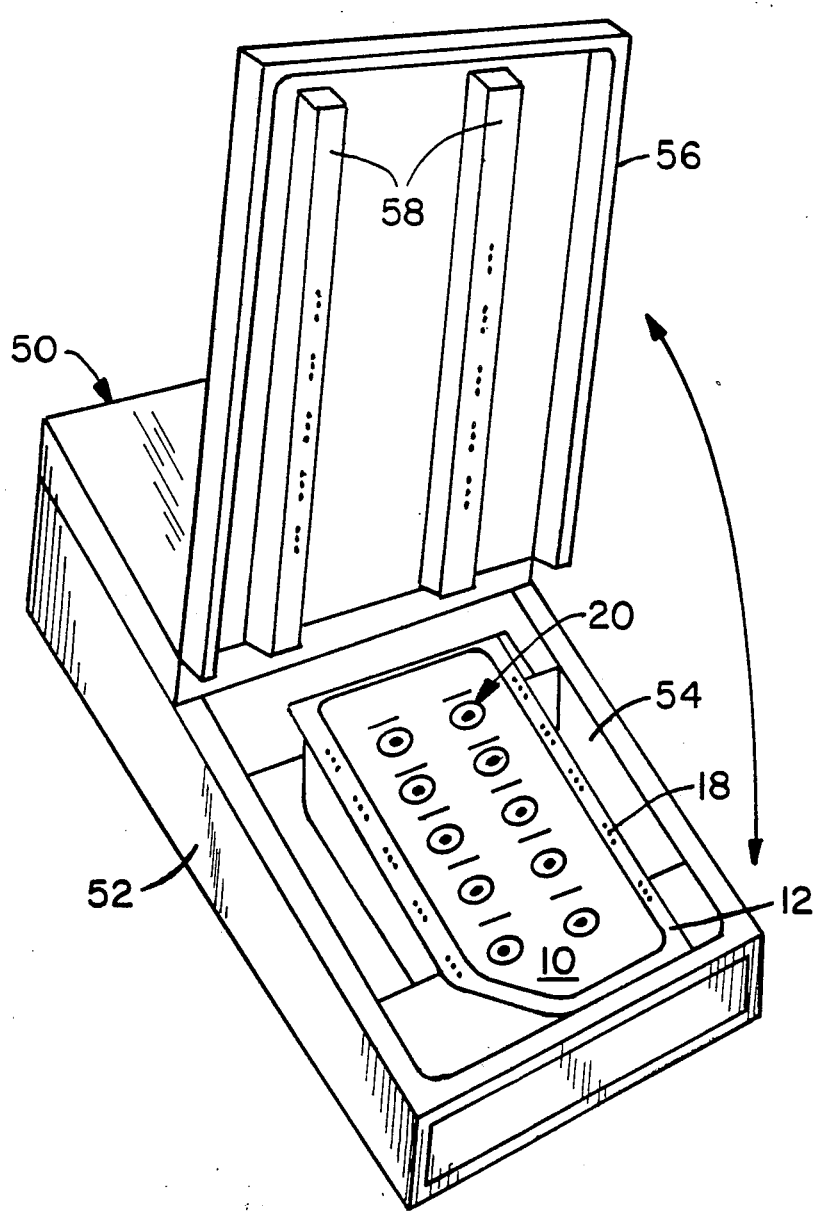
FIG. 5 is a view of the present apparatus.

The sensor apparatus (50) is shown in FIG. 5. Essentially, it is an ammeter (52) having a recessed sensor receiving area which is designed to receive the sensor (10) in a predetermined orientation. The sensor and the receiving area in FIG. 5 are notched in a complementary fashion such that the sensor can be inserted only in one way. A hinged ammeter cover (56) has a contact means (58) thereon such that when the lid is closed, the contact means engage the separate electrode leads and connect them in a conventional manner to the ammeter controls. Of course, the ammeter can be equipped with a programmable control such that one can either select the sequence of monitoring the current from the separate arrays or have a simultaneous monitoring of all of the arrays.

A second embodiment of the apparatus would eliminate the hinged lid. A slot could be provided that allows one to insert the sensor therein whereupon the contact means automatically engages the contact points on the sensor.

In a typical assay configuration, other preferable sensor features can be used. For example, if a glucose redox reaction is being monitored, one can provide a reagent pad (60) located above the array that has the electron transfer mediation located thereon. Also an array cover (30) can be located above the array and the pad to insure that either any liquid reagents do not evaporate or any solid reagents do not sublimate. If a plurality of arrays are used as in FIG. 1, one cover can extend over all the arrays.

IMMUNOASSAYS

EXAMPLE 1

The present sensor and apparatus can be used to perform immunoassays. The following example demonstrates an assay for the free thyroid hormone thyroxine ($T_4$). A graphite electrode array having a working electrode surface area of 200 $mm^2$ is coated with a 20 $\mu l$ aliquot of 1:75 collodion in a 0.5M ferrocene in methanol solution. The resulting layer is air dried at room temperature. Above this layer is deposited 50 $\mu g$ of a magnetic solid phase conjugate comprising MAGIC$^R$ magnetic particles from Ciba Corning Diagnostics Corp. coupled to a $T_4$ antibody (Ab($T_4$)). A 100 $\mu l$ sample of human serum containing $T_4$ and 10 $\mu l$ of a $T_4$ glucose oxidase conjugate ($T_4$-G.O.) are pipetted onto the electrode array. After ten minutes of incubation, 10 $\mu l$ of a 25% w/v glucose solution is added. The sensor is now ready to be read by the apparatus.

The apparatus comprises a conventional ammeter designed to supply a +0.40 V potential between the working electrode and the counter electrode. The counter electrode is maintained as a floating standard which maintains a constant voltage, between the other two electrodes. A positive current at the working electrode represents a reduction of the electron transfer mediator. A ferromagnet or an electromagnet is located in the sensor receiving area to be beneath the array.

Immediately after addition of the glucose, the sensor is placed in the sensor receiving area of the apparatus. The magnet pulls both the MAGIC$^R$-Ab($T_4$) · $T_4$-G.O. conjugate pair and the MAGIC$^R$-Ab($T_4$)·$T_4$ conjugate pair to the surface. The voltage is applied and the current read in microamperes. This immunoassay is homogeneous and competitive. The more $T_4$ present in the sample, the less enzyme bound to the working electrode through the first conjugate pair, and thus the less amperage.

EXAMPLE 2

The same procedure as in Example 1 is followed except a different conjugate and sample are used. More particularly, above the electrode array is deposited 50 $\mu g$ of a magnetic solid phase conjugate comprising MAGIC$^R$ magnetic particles from Ciba Corning Diagnostics Corp, coupled to an IgE antibody (Ab (IgE)). A 100 $\mu l$ sample of human serum containing IgE and 10 $\mu l$ of an IgE glucose oxidase conjugate (IgE-G.O.) are pippetted onto the electrode array. After ten (10) minutes of incubation, 10 $\mu l$ of a 25% w/v glucose solution is added.

The above apparatus of Example 1 measures the presence of IgE in the sample by means of the MAGIC$^R$-Ab(IgE)·IgE-G.O. conjugate pair which is pulled to the surface of the array.

Clinical Chemistry Assay

Clinical chemistry assays can be run as well with the present sensor and apparatus. Two generic methods use the measurement of $H_2O_2$ or the redox reasction of NADH. For example, it is envisioned that the following analytes can be detected by the present sensor using the listed enzyme in the same manner as glucose oxidase in the above Examples:

| Analyte | Enzyme in Conjugate |
|---|---|
| PEROXIDE DETECTION | |
| Alcohols | Alcohol oxidase |
| L-amino acids | L-amino acid oxidase |
| Cholesterol | Cholesterol Oxidase |
| Creatine | Creatine hydrolase |
| Creatine | Creatinase/sarcosine oxidase |
| Galactose | Galactose oxidase |
| Glucose | Glucose oxidase |
| Lactose | B-galactosidase/glucose oxidase |
| Maltose | Maltase/glucose oxidase |
| NADH REDOX DETECTION | |
| L-Glutamic acid | Glutamate dehydrogenase |
| Ethanol | Alcohol dehydrogenase |
| Lactic Acid | Lactage dehydrogenase |
| Malate | Malate dehydrogenase |
| Nitrate | Nitrate dehydrogenase |
| Phosphate | Phosphorylase/posphoglucomatase |

In the NADH redox assays, an electron transfer mediator is not required when an adequate potential is applied, such as +1.50 volts.

It should be apparent to one having ordinary skill in the art that many variations are possible without departing from the spirit and scope of the invention.

I claim:

1. A method for performing an immunoassay of an analyte in a blood or a blood component test sample on a unitary electrochemical sensor, the method comprising:
    (a) applying a test sample onto a unitary electrochemical sensor, said sensor comprising:
        (i) a sensor support member including an electrically non-conductive surface; and
        (ii) a plurality of wells deposited on the support member, wherein within each well is deposited an electrode array, the array defining an area on the support member for applying a test sample, the array consisting of a working electrode, a counter electrode and a reference electrode; and wherein the electrodes of the array are spaced from one another horizontally and vertically in said well, and wherein sensor activating chemicals are located on or attached to the working electrode of the array, the sensor activating chemicals comprising an electron transfer mediator, a first conjugate including a specific binding partner for the analyte to be measured, and a second conjugate including a known amount of the said analyte attached to an oxidizing catalyst or oxidizing substrate; and wherein the second conjugate is located on or attached to the working electrode of said array following the application of the test sample;
    (b) applying an electron source onto the array on which said test sample was applied;

(c) applying a preselected potential between the working electrode and the counter electrode of the array;

(d) measuring the current between the working electrode and the counter electrode of the array; and (e) determining the amount of the analyte in the test sample from the measurement of the current in step (d) relative to the preselected potential of step (c).

2. The method of claim 1, wherein said first conjugate and said second conjugate are attached to distinct magnetic particles.

3. The method of claim 2, wherein said magnetic particles are drawn to a magnet during the performance of said immunoassay; and wherein said magnet is located adjacent to the working electrode of the array.

4. The method of claim 3 wherein said magnet is a component of an apparatus, said apparatus being adapted to receive the unitary electrochemical sensor.

5. The method of claim 1, wherein said electron source is glucose; and wherein said oxidizing catalyst is glucose oxidase.

6. The method of claim 1, wherein said electron transfer mediator is ferrocene.

7. The method of claim 1, wherein said electron source is an immunoglobulin; and wherein said oxidizing catalyst is an immunoglobulin-glucose oxidase conjugate of the same immunoglobulin as said electron source.

8. The method of claim 1, wherein said analyte is an antibody or an antigen.

* * * * *